(12) United States Patent
Pawar et al.

(10) Patent No.: US 11,717,597 B2
(45) Date of Patent: Aug. 8, 2023

(54) SURFACE ALLOYED MEDICAL IMPLANT

(71) Applicant: Smith & Nephew, Inc., Memphis, TN (US)

(72) Inventors: Vivek Pawar, Germantown, TN (US); Donald E. Kramer, Memphis, TN (US); Carolyn L. Weaver, Memphis, TN (US); Shilesh C. Jani, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 728 days.

(21) Appl. No.: 16/860,471

(22) Filed: Apr. 28, 2020

(65) Prior Publication Data

US 2020/0254145 A1 Aug. 13, 2020

Related U.S. Application Data

(62) Division of application No. 12/811,672, filed as application No. PCT/US2009/030021 on Jan. 2, 2009, now Pat. No. 10,675,384.

(Continued)

(51) Int. Cl.
*A61L 27/50* (2006.01)
*A61L 27/04* (2006.01)
*A61L 27/30* (2006.01)

(52) U.S. Cl.
CPC ............... *A61L 27/50* (2013.01); *A61L 27/04* (2013.01); *A61L 27/306* (2013.01); *A61L 2400/18* (2013.01)

(58) Field of Classification Search
CPC ........... A61L 27/50; A61L 27/30; A61L 27/04
(Continued)

(56) References Cited

U.S. PATENT DOCUMENTS 5,372,660 A 12/1994 Davidson et al.
2002/0042656 A1 4/2002 Hunter et al.
(Continued)

FOREIGN PATENT DOCUMENTS

GB 1187247 A 4/1970
GB 1200165 A 7/1970
(Continued)

OTHER PUBLICATIONS

European Examination Report (2nd); European Patent Office; European Application No. 09700845.2; dated Oct. 20, 2016; 6 pages.
(Continued)

*Primary Examiner* — Matthew W Schall
(74) *Attorney, Agent, or Firm* — KDW Firm PLLC (57) ABSTRACT

A medical implant is disclosed. The medical implant includes: a first biocompatible metal forming a substrate (210, 310, 410), a second biocompatible metal diffused into the first biocompatible metal to form an biocompatible alloy surface (220, 314, 414), the alloy surface further including a diffusion hardening species, wherein the diffusion hardening species may be carbon, nitrogen, oxygen, boron, or any combination thereof. A method of forming a medical implant is also disclosed. The method includes the steps of: providing a first biocompatible metal or alloy that forms a substrate (210, 310, 410), providing a second biocompatible metal or alloy, diffusing the second biocompatible metal into the first biocompatible metal to form an alloy layer (220, 314, 414), removing excess second metal material from the substrate to expose the alloy layer, and diffusion hardening the alloy layer.

11 Claims, 4 Drawing Sheets

Related U.S. Application Data (60) Provisional application No. 61/019,075, filed on Jan. 4, 2008.

(58) Field of Classification Search
 IPC ........................................................ A61L 27/50
 See application file for complete search history.

(56) References Cited

U.S. PATENT DOCUMENTS

| | | |
|---|---|---|
| 2003/0125808 A1 | 7/2003 | Hunter et al. |
| 2004/0122524 A1 | 6/2004 | Hunter et al. |
| 2005/0031663 A1 | 2/2005 | Larsson et al. |
| 2006/0161256 A1 | 7/2006 | Ziegler et al. |
| 2006/0233944 A1 | 10/2006 | Papoola et al. |
| 2007/0137734 A1 | 6/2007 | Pawar et al. |
| 2008/0300682 A1 | 12/2008 | Rivard et al. |

FOREIGN PATENT DOCUMENTS

| | | |
|---|---|---|
| JP | S55-69250 A | 5/1980 |
| JP | S61-064871 A | 4/1986 |
| JP | H01-100298 A | 4/1989 |
| JP | H07-148244 A | 6/1995 |
| JP | 2005-538745 A | 12/2005 |
| JP | 2006-511272 A | 4/2006 |
| JP | 2007-254856 A | 10/2007 |
| JP | 2009-519750 A | 5/2009 |
| WO | 2009/026277 A2 | 2/2009 |

OTHER PUBLICATIONS

Australian Examination Report; Australian Patent Office; Australian Patent Application No. 2016269495; dated Sep. 6, 2017; 2 pages.

Australian Patent Examination Report No. 2; Australian Patent Office; Australian Patent Application No. 2015201857; dated Jun. 17, 2016; 2 pages.

Australian Patent Examination Report No. 1; Australian Patent Office; Australian Patent Application No. 2015201857; dated Oct. 21, 2015; 2 pages.

First Examination Report; Government of India Patent Office; Indian Patent Application No. 4787/DELNP/2010; Sep. 29, 2015; 2 pages.

Notice of Reasons for Rejection; Japanese Patent Office; Japanese Patent Application No. 2010-541573; dated Feb. 3, 2014; 5 pages.

First European Office Action; European Patent Office; European Patent Application No. 09700845.2; dated May 8, 2013; 7 pages.

Second Office Action; Chinese Patent Office; Chinese Patent Application No. 200980107981.7; dated May 22, 2015; 7 pages.

Decision on Rejection; Chinese Patent Office; Chinese Patent Application No. 200980107981.7; dated Oct. 12, 2013; 8 pages.

Japanese First Office Action issued in Japanese Application No. 2010-541573, dated Feb. 26, 2013, 7 pages.

Chinese First Office Action issued in Chinese Application No. 200980107981.7, dated Dec. 13, 2012, 17 pages.

International Search Report and Written Opinion issued for PCT/US2009/030021, dated Jul. 30, 2009, 9 pages.

SURFACE ALLOYED MEDICAL IMPLANT

CROSS-REFERENCE TO RELATED APPLICATION

This application is a divisional of pending U.S. patent application Ser. No. 12/811,672, filed Sep. 28, 2010, which application is a National Phase Application of International Application No. PCT/US2009/030021, filed Jan. 2, 2009, which claims the benefit of U.S. Provisional Application No. 61/019,075, filed on Jan. 4, 2008. The disclosure of each prior application is incorporated by reference in their entirety.

BACKGROUND OF THE INVENTION

1. Field of the Invention

The present invention relates generally to implantable prosthesis and more particularly to a surface alloyed medical implant.

2. Related Art

Medical implant materials, in particular orthopaedic implant materials, must combine high strength, corrosion resistance and tissue compatibility. The longevity of the implant is of prime importance especially if the recipient of the implant is relatively young because it is desirable that the implant function for the complete lifetime of a patient. Because certain metal alloys have the required mechanical strength and biocompatibility, they are ideal candidates for the fabrication of prostheses. These alloys include, as examples, 316 L stainless steel, chrome-cobalt-molybdenum alloys (CoCr), and titanium alloys.

Orthopaedic implant bearing components, also referred to as "couples," may be loosely classified as either: (a) hard-on-hard; or (b) hard-on-soft. In a hard-on-hard application, the material articulates against itself or another material of roughly the same or greater hardness. In contrast, a hard-on-soft application includes a first material articulating against a softer one. An example of a hard-on-hard application is two metal components articulating against one another, and an example of a hard-on-soft application is a metal component articulating against a polyethylene insert.

Currently, there are two primary types of hard-on-hard hip implant bearing components that are available commercially, namely metal-on-metal and ceramic-on-ceramic. The current standard material of metal-on-metal implants is high carbon cobalt chrome (CoCr) alloy. The major concern with the metal-on-metal implant is the metal ion release from the prosthesis and its unknown effects on the physiology of the human body. The advantage of metal-on-metal implants is that they can be used in larger sizes. The larger size of the implant allows greater range of motion and stability of the implant.

The metal-on-metal implants also have been shown to be useful for resurfacing type of application where conservation of bone is desired. In such larger joints, the conventional or cross-linked polyethylene is not preferred and metal-on-metal may be the only choice available. The larger size requires polyethylene liner to be thinner. A thinner liner may not be mechanically strong, may creep more or may lead to increased wear and osteolysis and eventually failure of the implant.

The other commonly used hard-on-hard implant material is ceramic-on-ceramic. The current standard material of ceramic-on-ceramic implants is alumina. The surface hardness of the alumina is approximately 20 to 30 GPa. Metal ion release is typically not a concern for these implants. But due to limited toughness and the brittle nature of ceramics, it is difficult to make these implants in larger sizes. The ceramic components have finite probability of fracture, thus leading to a potential joint failure and complications associated with the fracture of a joint.

Figure 1:
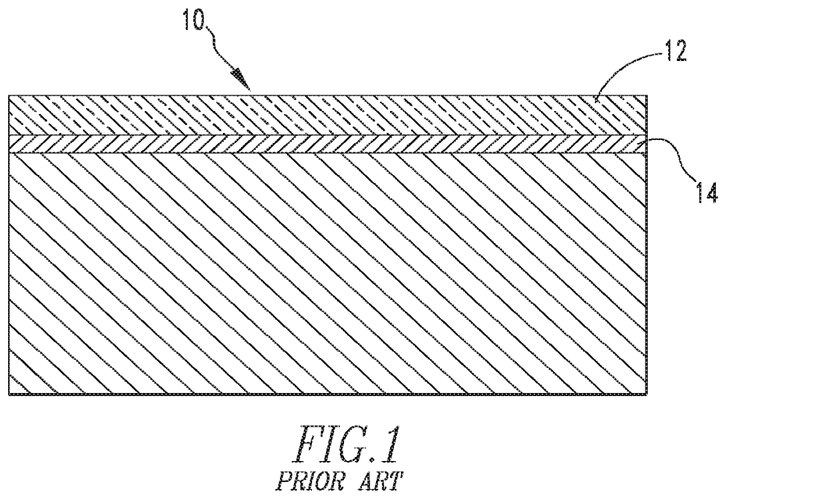
FIG. 1 is a schematic of an oxidized zirconium sample.
Figure 2:
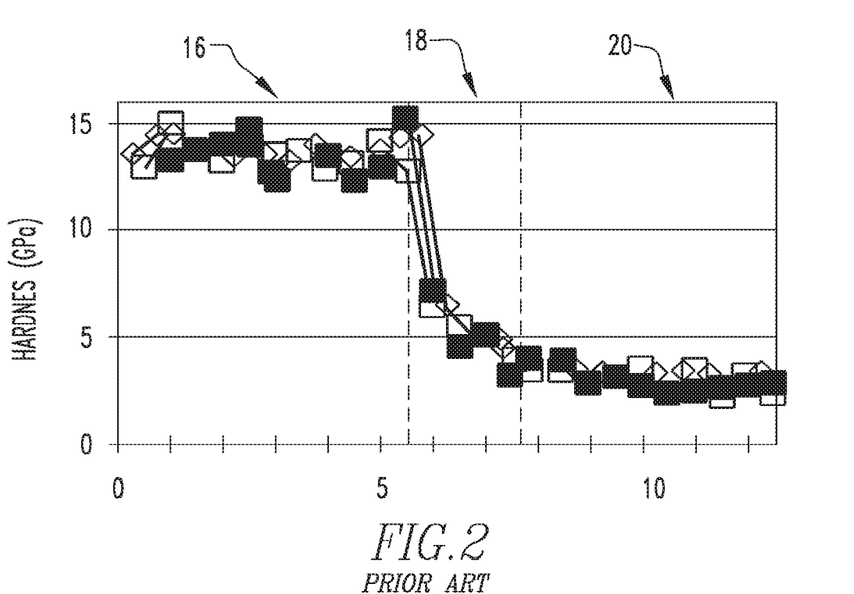
FIG. 2 illustrates a hardness profile an oxidized zirconium sample.

More recently, treated zirconium alloys have proven to be the most suitable materials for the fabrication of load-bearing and non-load bearing prostheses. Zirconium alloys are typically soft, and the hardness of such alloys can typically range from one and one-half to three GPa. Because these alloys are soft, they can be easily abraded with a harder material. The abrasion resistance of zirconium alloys, however, can be significantly improved by oxidizing or nitriding these alloys. The oxidized zirconium implant typically has a five to six micron thick ceramic surface of zirconium oxide that is formed by a thermally driven diffusion process in air. Beneath the zirconium oxide is a hard, oxygen-rich diffusion layer of approximately one and one-half to two microns. Beneath the diffusion zone is the softer zirconium alloy matrix. The hardness of the zirconium oxide surface is approximately 12 GPa. The significant reduction in wear of polyethylene against oxidized zirconium surfaces is attributed to the harder nature of the oxide ceramic. FIG. 1 illustrates a schematic cross-sectional view of an oxidized zirconium structure 10 with a zirconium oxide layer 12 and a diffusion hardened zone 14, which has a thickness of less than two microns. FIG. 2 illustrates a hardness profile of an oxidized zirconium structure having a ceramic oxide portion 16, an oxygen-rich diffusion zone 18, and a metal substrate 20. FIG. 2 is taken from M. Long, L. Reister and G. Hunter, Proc. 24th Annual Meeting of the Society For Biomaterials, Apr. 22-26, 1998, San Diego, Calif., USA.

U.S. Pat. No. 2,987,352 to Watson discloses a method of producing a blue-black oxide coating on zirconium alloy parts for the purpose of increasing their abrasion resistance. Both U.S. Pat. Nos. 2,987,352 and 3,615,885 produce a zirconium oxide coating on zirconium alloy by means of air oxidation. U.S. Pat. No. 3,615,885 continues the air oxidation long enough to produce a beige coating of greater thickness than the blue-black coating of U.S. Pat. No. 2,987,352. This beige coating does not have the wear resistance of the blue-black coating and is thus not applicable to many components where there are two work faces in close proximity The beige coating wears down more quickly than the blue-black oxide coating with the resulting formation of oxidized zirconium particles and the loss of the integrity of the oxidized zirconium surface. With the loss of the oxide surface the zirconium metal is then exposed to its environment and can lead to transport of zirconium ions into the adjacent environment.

The blue-black coatings have a thickness which is less than that of the beige coating although the hardness of the blue-black coating is higher than that of the beige coating. This harder blue-black oxide coating lends itself better to surfaces such as prosthetic devices. Although the blue-black coating is more abrasion resistant than the beige coating it is a relatively thin coating. It is therefore desirable to produce new and improved compositions that maintain the desirable properties of the blue-black coatings of the prior art (for example, increased abrasion resistance).

U.S. Pat. No. 5,037,438 to Davidson discloses a method of producing zirconium alloy prostheses with an oxidized zirconium surface. U.S. Pat. No. 2,987,352 to Watson discloses a method of producing zirconium bearings with an oxidized zirconium surface. The oxide coating produced is not always uniform in thickness and the non-uniformity reduces the integrity of the bonding between the zirconium alloy and the oxide layer and the integrity of the bonding within the oxide layer. Both U.S. Pat. Nos. 2,987,352 and 5,037,438 are incorporated by reference as though fully set forth herein.

While oxidized zirconium has been a great advancement over the conventional cobalt chromium and stainless steel alloys, there is still room for improvement. The totality of hardened zones, which is the oxide plus the diffusion hardened alloy, render the implant resistant to microscopic abrasion (for example, from third bodies such as bone cement, bone chips, metal debris, etc.) and slightly less resistant to macroscopic impact (surgical instrumentation and from dislocation/subluxation contact with metallic acetabular shells). In a hard-on-hard application, such as in a hip joint, the material articulates against itself or another hardened or non-hardened metal instead of polyethylene. The wear rates in such types of implants could be as high as one micron per year. With the totality of the hardened zone having a thickness of less than seven microns, previous oxidized zirconium implants are less than optimal for hard-on-hard applications due to longevity concerns.

U.S. Pat. No. 6,726,725 teaches that the oxide thickness can be increased up to 20 microns for hard-on-hard applications but oxide compositions having such thicknesses, although highly wear-resistant, can have significant number of oxide layer defects. Such defects can lead to localized spalling of the oxide. Also, the oxidized zirconium structure has a relatively small diffusion hardened zone, which makes them less than ideal for hard-on-hard applications. U.S. Pat. No. 6,726,725 is herein incorporated by reference.

U.S. patent application publication No. 2007/0137734 A1 teaches the use of a post oxidation vacuum treatment to increase the depth of hardening. This treatment allows oxygen from the oxide to diffuse into the substrate, and thus increase the depth of hardening, perhaps as much as 50 microns. Although this is a significant improvement over the previous oxidized zirconium structures, it should be noted that the depth of hardening is increased by increasing the thickness of the diffusion hardened metallic zone. Thus, if the oxide wears through, the diffusion hardened zone is the bearing portion during the remainder of the life of the product. In a hard-on-hard application, the oxide wear debris is expected to be more inert than the metallic diffusion hardened wear debris but still this metallic wear debris may thus result in some ion release.

One of the ways to reduce the oxide wear is to form a zirconium nitride instead of zirconium oxide. Zirconium nitride is slightly harder than the zirconium oxide and thus may lead to reduced wear. U.S. Pat. No. 5,399,207 describes a method to make oxidized or nitrided zirconium compositions using a fluidized bed furnace. The '207 patent states that the nitridation can be carried out from 700 degrees C. to 870 degrees C. The '207 patent teaches use of pure nitrogen instead of air or oxygen to achieve the nitridation of the surfaces. U.S. Pat. No. 5,180,394 to Davidson discloses orthopedic implants with blue-black zirconium oxide or zirconium nitride surfaces. The '394 patent teaches that the nitride layer to be formed at 800 degrees C. in about one hour in nitrogen atmosphere. Use of such high temperature can lead to microstructural changes such as grain growth. These changes in-turn may affect the mechanical properties of the substrate. Higher temperature process can also dimensionally distort the components being manufactured. It should be noted that the zirconium nitride may not adhere as well as zirconium oxide does to the zirconium alloy substrate. It should also be noted that in the entire prior art, there has been disclosed attempts to make either a zirconium oxide or a zirconium nitride but not a combination. U.S. Pat. Nos. 5,399,207 and 5,180,394 are herein incorporated by reference.

U.S. Patent Application Publication No. 2006/0233944A1 teaches treating cobalt chrome (CoCr) with zirconium ions in a vacuum process, known as Ion Beam Assisted Deposition (IBAD), and then oxidizing the same. One drawback of such process is that most of the zirconium will deposit as a coating and only a very small fraction will get alloyed into a substrate alloy. The oxidation step thereafter forms zirconium oxide as a coating on the surface of the CoCr alloy. The potential drawback of this process is that the integrity of such formed zirconium oxide may not be as good as it is physically bonded to the surface. Also the zirconium oxide thickness suggested by the '944 application is only three to five microns thick. Such thin surface will be less than optimal for hard-on-hard applications.

SUMMARY OF THE INVENTION

The invention is a new composition and medical implants made therefrom. The composition includes an alloyed surface on the medical implant. In one embodiment, the alloyed surface is created by diffusing one or more metallic species and then treating it thereafter to form a ceramic surface. The invention includes orthopedic implants made from the new composition, methods of making the new composition, and methods of making orthopedic implants from the new composition. The composition has application, for example, in articulating and non-articulating surfaces of medical implants. While the composition is particularly well-suited for hard-on-soft applications, the invention also encompasses the use of this medical implant composition in hard-on-hard applications, such as in a hip, knee, spinal, or other implants.

According to some aspects of the present invention, there may be provided a medical implant comprising: a first component, said first component comprising a substrate, said substrate comprising a first biocompatible metal; a surface alloyed zone on at least a portion of said substrate, said surface alloyed zone comprising: a surface alloyed/non-hardened zone comprising a second biocompatible metal on a least a portion of said substrate; a surface alloyed/hardened zone comprising a diffusion hardening species is selected from the group consisting of carbon, nitrogen, oxygen, boron, and any combination thereof; and optionally, a second component in contact with said first component.

According to some embodiments of the present invention, at least one of the first biocompatible metal and the second biocompatible metal is commercially pure.

According to some embodiments of the present invention, the first biocompatible metal is selected from the group consisting of titanium, zirconium, tantalum, and niobium.

According to some embodiments of the present invention, the second biocompatible metal is selected from the group consisting of titanium, zirconium, tantalum, and niobium.

According to some embodiments of the present invention, the surface alloyed/hardened zone comprises a ceramic.

According to some embodiments of the present invention, the surface alloyed zone has a thickness that ranges from about 5 to about 100 microns.

According to some embodiments of the present invention, the surface alloyed zone has a thickness that ranges from about 20 to about 100 microns.

According to some embodiments of the present invention, the surface alloyed zone has a thickness which ranges from about 50 to about 100 microns.

According to some embodiments of the present invention, at least one of the first biocompatible metal and the second biocompatible metal is an alloy.

According to some embodiments of the present invention, the alloy is selected from the group consisting of zirconium, cobalt, chromium, titanium, niobium, aluminum, vanadium, tantalum, and combinations thereof.

According to some aspects of the present invention, there may be provided a method of forming a medical implant comprising: providing a substrate comprising a first biocompatible metal; diffusing a second biocompatible metal into the first biocompatible metal to form an surface alloyed zone on at least a portion of said substrate; and diffusion hardening at least a portion of said surface alloyed zone with a diffusion hardening species selected from the group consisting of carbon, nitrogen, oxygen, boron, and any combination thereof, to form a surface alloyed/hardened zone within a least a portion of said surface alloyed zone.

According to some embodiments of the present invention, said first biocompatible metal is an alloy.

According to some embodiments of the present invention, the step of diffusing a second biocompatible metal is carried out in a vacuum of less than $10^{-4}$>Torr and in the temperature range from 600 degrees C. to 1200 degrees C.

According to some embodiments of the present invention, the step of diffusion hardening is carried out in presence of a gas selected from the group consisting of oxygen, nitrogen, and carbon.

According to some embodiments of the present invention, the method further includes a step of removing a portion of said second biocompatible metal, said step of removing is selected from the group consisting of grinding, tumbling, glass-beading, shot-peening, grit blasting, polishing, sanding, and through the use of abrasive slurry.

According to some embodiments of the present invention, the step of diffusing a second biocompatible metal is carried out in an inert gas atmosphere.

According to some embodiments of the present invention, the inert gas is selected from the group consisting of argon, helium, nitrogen and any combinations thereof.

According to some embodiments of the present invention, said step of diffusing a second biocompatible metal comprises applying a focused energy source to said substrate. According to some embodiments of the present invention, said focused energy source comprises a laser. According to some embodiments of the present invention, said focused energy source comprises an induction heating source.

According to some aspects of the present invention, there may be provided a medical implant comprising: a first cooperating component and a second cooperating component, wherein the first cooperating component, the second co-operating component, or both comprise: a surface alloyed zone on at least a portion of said substrate, said surface alloyed zone comprising: a surface alloyed/non-hardened zone comprising a second biocompatible metal on a least a portion of said substrate; a surface alloyed/hardened zone comprising a diffusion hardening species is selected from the group consisting of carbon, nitrogen, oxygen, boron, and any combination thereof.

According to some aspects of the present invention, there may be provided a medical implant comprising: a first biocompatible metal forming a substrate; a second biocompatible metal diffused into said first biocompatible metal to form a biocompatible alloy surface, the alloy surface formed in (b) further comprising a diffusion hardening species, wherein said diffusion hardening species is selected from the group consisting of carbon, nitrogen, oxygen, boron, and any combination thereof.

According to some embodiments of the present invention, at least one of the first biocompatible metal and the second biocompatible metal is commercially pure.

According to some embodiments of the present invention, the first biocompatible metal is selected from the group consisting of titanium, zirconium, tantalum, and niobium.

According to some embodiments of the present invention, the second biocompatible metal is selected from the group consisting of titanium, zirconium, tantalum, and niobium.

According to some embodiments of the present invention, the diffusion hardened alloy surface is a ceramic.

According to some embodiments of the present invention, a thickness of the alloy surface ranges from about 5 to about 100 microns.

According to some embodiments of the present invention, a thickness of the alloy surface ranges from about 20 to about 100 microns.

According to some embodiments of the present invention, a thickness of the alloy surface ranges from about 50 to about 100 microns.

According to some embodiments of the present invention, at least one of the first biocompatible metal and the second biocompatible metal is an alloy.

According to some embodiments of the present invention, the alloy is selected from the group consisting of zirconium, cobalt, chromium, titanium, niobium, aluminum, vanadium, tantalum, and combinations thereof.

According to some aspects of the present invention, there may be provided a medical implant comprising: a first portion comprising a metal substrate made of a first biocompatible metal; and a diffusion hardened second portion comprising an alloy layer comprised of at least the first biocompatible metal and a second biocompatible metal.

According to some embodiments of the present invention, at least one of the first biocompatible metal and the second biocompatible metal is an alloy.

According to some aspects of the present invention, there may be provided a method of forming a medical implant comprising: providing a first biocompatible metal that forms a substrate; providing a second biocompatible metal; diffusing the second biocompatible metal into the first biocompatible metal to form an alloy layer; removing excess second metal material from the alloy layer; and diffusion hardening the alloy layer.

According to some embodiments of the present invention, at least one of the first biocompatible metal and the second biocompatible metal is an alloy.

According to some embodiments of the present invention, the step of diffusion hardening the alloy layer is carried out in presence of a gas selected from the group consisting of oxygen, nitrogen, and carbon.

According to some embodiments of the present invention, the step of removing excess second material from the substrate to expose the alloy layer includes the step selected from the group consisting of grinding, tumbling, glass-beading, shot-peening, grit blasting, polishing, sanding, and through the use of abrasive slurry.

According to some embodiments of the present invention, the step of diffusion hardening the alloy layer includes the step of diffusion hardening with a diffusion hardening species, wherein said diffusion hardening species is selected from the group consisting of carbon, nitrogen, oxygen, boron, and any combination thereof.

According to some embodiments of the present invention, the step of diffusing the second biocompatible metal into the first biocompatible metal to form an alloy layer is carried out in a vacuum of less than $10^{-4}$ Torr.

According to some embodiments of the present invention, the step of diffusing a second biocompatible metal is carried out in a temperature range from 600 degrees C. to 1200 degrees C.

According to some embodiments of the present invention, the second biocompatible metal is in powder form. According to some embodiments of the present invention, a thickness of each powder particle ranges from about 500 to about 2000 microns.

According to some embodiments of the present invention, the step of diffusing the second biocompatible metal into the first biocompatible metal to form an alloy layer is carried out in an inert gas.

According to some embodiments of the present invention, the inert gas is selected from the group consisting of argon, helium, nitrogen and any combinations thereof.

According to some aspects of the present invention, there may be provided a method of forming a medical implant comprising: providing a first biocompatible metal that forms a substrate; providing a second biocompatible metal; treating the second biocompatible metal and the first biocompatible metal with focused energy to form an alloy layer; removing excess second metal material from the substrate to expose the alloy layer; and diffusion hardening the alloy layer.

According to some embodiments of the present invention, the step of treating the second biocompatible metal and the first biocompatible metal with focused energy to form an alloy layer includes the use of a laser.

According to some embodiments of the present invention, the step of treating the second biocompatible metal and the first biocompatible metal with focused energy to form an alloy layer includes the use of induction heating.

According to some aspects of the present invention, there may be provided a medical implant comprising: a first co-operating component and a second co-operating component, wherein the first co-operating component, the second co-operating component, or both comprise: a first biocompatible metal forming a substrate; and a second biocompatible metal diffused into said first metal to form an alloy surface, the alloy surface further comprising a diffusion hardening species, wherein said diffusion hardening species is selected from the group consisting of carbon, nitrogen, oxygen, boron, and any combination thereof.

According to some embodiments of the present invention, at least one of the first biocompatible metal and the second biocompatible metal is an alloy.

According to some embodiments of the present invention, the diffusion hardened alloy surface is a ceramic.

According to some embodiments of the present invention, the first and second co-operating components form a medical device selected from the group consisting of a hip implant, a knee implant, a spine implant, and a shoulder implant.

In one embodiment, a surface of a CoCr alloy is diffused with zirconium at high temperature using a conventional diffusion process. The alloy is then oxidized to form a zirconium oxide mixed with cobalt and chromium oxide on the surface of the CoCr alloy.

In another embodiment, a surface of a Ti-6Al-4V alloy is diffused with zirconium at high temperature using a conventional diffusion process. The alloy is then oxidized to form mixed oxides of titanium, zirconium, aluminum and potentially vanadium.

In another embodiment, titanium is diffused in zirconium alloy. Then the entire sample is oxidized. Diffusion of titanium in the zirconium substrate results in forming a much thicker oxide on the surface than it would have formed otherwise on a non-alloyed zirconium surface. The treated alloy can then be further diffusion hardened with a vacuum treatment to increase the depth of hardening.

In another embodiment, chromium is diffused into the cobalt chrome substrate and then the surface is nitrided to form a chromium nitride or is oxidized to form chromium oxide.

Further areas of applicability of the invention will become apparent from the detailed description provided hereinafter. It should be understood that the detailed description and specific examples, while indicating the particular embodiment of the invention, are intended for purposes of illustration only and are not intended to limit the scope of the invention.

BRIEF DESCRIPTION OF THE DRAWINGS

The accompanying drawings, which are incorporated in and form a part of the specification, illustrate the embodiments of the present invention and together with the written description serve to explain the principles, characteristics, and features of the invention. In the drawings.

DETAILED DESCRIPTION OF THE EMBODIMENTS

The following description of the depicted embodiment(s) is merely exemplary in nature and is in no way intended to limit the invention, its application, or uses.

As used herein, "a" or "an" means one or more. Unless otherwise indicated, the singular contains the plural and the plural contains the singular.

As used herein, the term "alloy" means a metallic solid solution. The term "surface alloy" is defined as an alloy in which one or more alloying species is present in a surface and a near-surface region in a greater concentration than in the bulk substrate. As such, the surface and the near-surface region include one or more "surface alloy species." Thus, a bulk sample of Zr-2.5Nb is an alloy of zirconium having niobium at 2.5% throughout. If that same sample is then surface alloyed with titanium such that titanium is present in greater concentration in the surface and the near-surface region than in the substrate, the sample is an "alloy" and has a "surface alloy."

As used herein, "zirconium alloy" is defined broadly, and includes alloys having at least 5% (w/w) zirconium. The alloys can be of zirconium, titanium, hafnium and niobium.

The alloys can be polycrystalline or amorphous or single crystals or combinations of same.

The "surface alloyed zone" is defined as the surface and the near-surface region that comprises one or more surface alloying metallic species. In some embodiments, the surface alloyed zone region may be about one to about five percent of the thickness of the substrate, and more particularly from about one to about two percent of the thickness of the substrate. In some embodiments, the surface alloyed zone may have a thickness from about 10 microns to about 2000 microns. For example, if the substrate is 10 mm thick then the surface alloyed zone may be as thick as 2 mm. In one particular embodiment, the surface alloyed zone may have a thickness from about 10 microns to about 100 microns.

The "diffusion hardened zone" is defined as the surface alloyed zone that comprises one or more diffusion hardening species. Examples of diffusion hardening species include carbon, oxygen, nitrogen, boron, or any combination thereof. The diffusion hardened zone has hardness at least 1.1 times greater than the substrate hardness. Where a composition has been both surface alloyed with one or more alloying species and diffusion hardened with one or more diffusion hardening species, the region that comprises both a diffusion hardening species and a surface-alloying metal is defined as the "surface alloyed/hardened zone." In many embodiments of the present invention, the diffusion hardening is performed such that any diffusion hardening species do not extend as far into the substrate as do the surface alloying species. The region at depths that comprises only surface alloying species but no diffusion hardening species is defined as the "surface alloyed/non-hardened zone." In such cases, the surface alloyed zone comprises both the surface alloyed/hardened zone and the surface alloyed/non-hardened zone.

As used herein, "ceramic" is defined as a chemical compound of a metal (or a metal constituent in an alloy) and one or more non-metals, including carbon, oxygen, nitrogen, boron, and combinations thereof. While the preferred embodiment of the ceramic of the present invention is an oxide, the ceramic of the present invention includes oxides, carbides, nitrides, borides, and any combination thereof. As used herein, "ceramic layer" is defined as a stratum of material consisting of ceramic which forms a part of a greater material. As used herein, the term "ceramic coating" refers to a surface transformed layer, surface film, surface oxide, nitride, carbide, boride (or combination thereof) present on the alloy or metal substrate.

As used herein, "biocompatible metal or biocompatible alloy" is defined as the individual metals or metal combinations (alloy) that are currently used in orthopedic industry. An example of biocompatible metal is pure titanium or pure zirconium with any additional metals less than 1 wt %. Examples of biocompatible alloys include cobalt-chromium-molybdenum, titanium-aluminum-vanadium, nickel-titanium and zirconium-niobium. The other biocompatible alloys that are referred in this invention are the alloys that are made from either zirconium or titanium or tantalum or niobium or hafnium or combination thereof.

In one embodiment of the invention, the composition that comprises the implant is made by a process that includes the steps of providing a first metal that forms a substrate, diffusing a second metal into the metal substrate, removing excess coating material from the first metal to provide an alloyed surface of the substrate, and hardening the alloyed surface. As examples, the first metal may be made of cobalt chrome, titanium, titanium alloy, stainless steel, zirconium, or zirconium alloy. As examples, the second metal may be made of zirconium, cobalt, chromium, titanium, niobium, aluminum, vanadium, or combinations thereof. As examples, the excess coating material may be removed by grinding, tumbling, glass-beading, shot-peening, grit blasting, polishing, sanding, or through the use of abrasive slurry. The hardening step may include treating the surface in an atmosphere of oxygen, carbon, nitrogen, boron, or any combination thereof.

In one particular embodiment of the invention, a substrate of a biocompatible alloy, such as Zr-2.5 Nb, has a surface characterized by a ceramic layer that includes zirconium and titanium. The thickness of the ceramic layer is generally from about 1 micron to about 100 microns.

Figure 3:
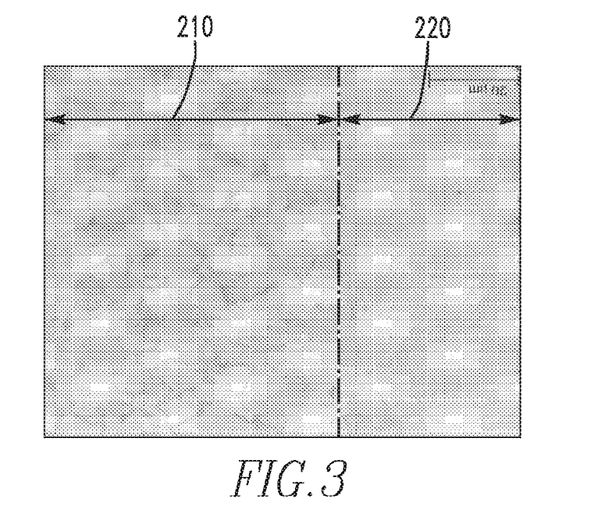
FIG. 3 illustrates the depth of titanium diffusion in a sample of Zr-2.5 Nb alloy surface alloyed with titanium.

In one particular method, commercially pure titanium powder is laid on or placed upon a surface of an Zr-2.5 Nb alloy sample. The sample and the titanium powder are then heated to about 800 degrees C. for about 10 hours in vacuum, which may be, as an example, less than about $10^{-4}$ torr. After the treatment, the sample is cooled to room temperature and the excess titanium surface powder is removed. This results in a surface alloy on the substrate, which is illustrated in a metallographic image in FIG. 3. The embodiment depicted in FIG. 3 illustrates a composition in cross-section having a substrate 210 and a surface alloyed zone 220. It should be noted that based on the metallographic image it appears that there is a distinct boundary between the substrate 210 and the surface alloyed zone 220. However, those having ordinary skill in the art would understand that such a distinct boundary does not exist. The titanium concentration gradually changes from the surface alloyed zone 220 to the substrate 210, even though metallographically it is not visible.

Figure 4:
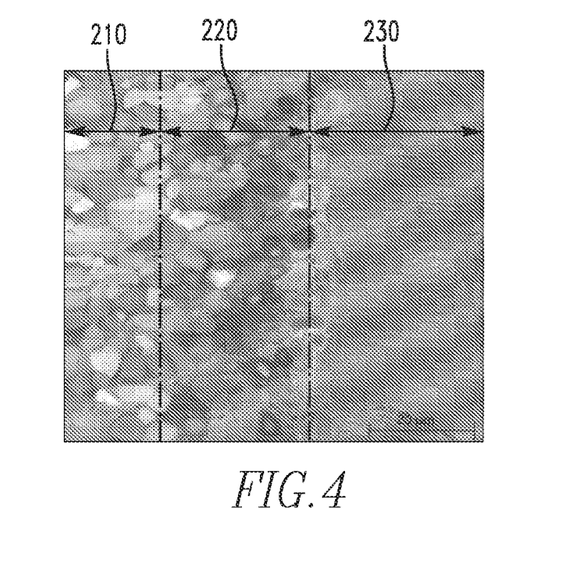
FIG. 4 is a metallographic image of a Zr-2.5 Nb sample surface alloyed with titanium and then oxidized.

Thereafter, the sample with the alloyed surface may be hardened. For example, the alloy surface may be diffusion hardened, such as by oxidization at about 600 degrees C. for about one hour and 15 minutes. Those having ordinary skill in the art would understand that nitriding, carburizing, or other similar treatments may equally be used. The alloy surface after oxidation is illustrated by the metallographic image in FIG. 4. The embodiment depicted in FIG. 4 illustrates a composition in cross-section having the substrate 210, the surface alloyed/non-hardened zone 220, and a surface alloyed/hardened zone 230. In the depicted embodiment, the surface alloyed/hardened zone 230 is an oxide layer. In the embodiment depicted in FIG. 4, the oxidation process provides an approximately 25 micron thick oxide on the surface. This is significant as the titanium diffusion into the substrate provides a surface that forms a thicker oxide than that could be achieved otherwise on a Zr-2.5 Nb substrate without such Ti alloyed region. For a non-alloyed surface, the oxide thickness generally would be about five to six microns in thickness.

Figure 5:
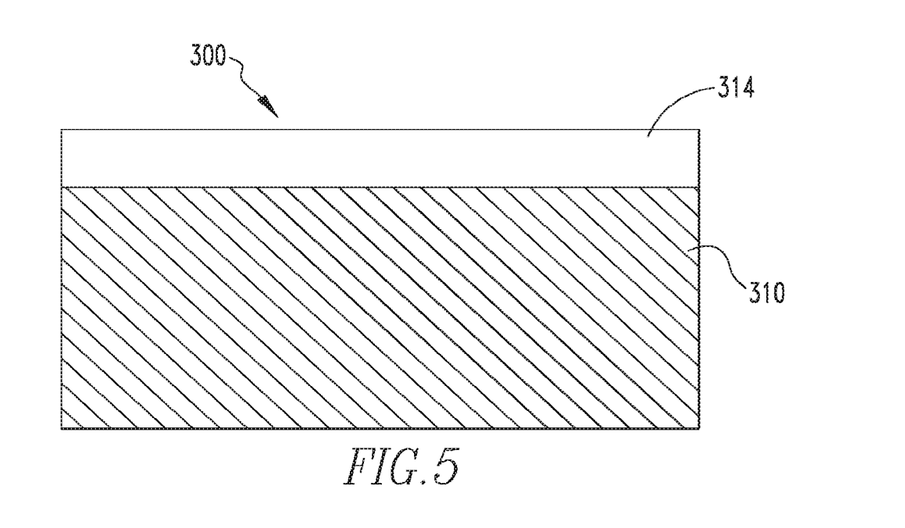
FIG. 5 is a schematic of a cobalt chrome surface alloyed with zirconium and subsequently oxidized.

FIG. 5 illustrates another embodiment of the invention. The embodiment depicted in FIG. 5 is a structure 300 having a substrate 310 and a surface alloyed zone 314. In FIG. 5, a mixture of oxides, nitrides, carbides or any combinations thereof covers a substrate of a biocompatible alloy, such as CoCr. The mixture may be formed by diffusing one or more of zirconium, titanium, cobalt and chromium into the substrate. The thickness of the mixed oxides is generally about 1 micron to about 100 microns. As an example of the first embodiment, a surface of a CoCr alloy is diffused with zirconium at high temperature using a conventional diffusion process. The alloy is then oxidized to form a zirconium oxide mixed with cobalt and chromium oxide on the surface of the CoCr alloy.

In another embodiment, a surface of a Ti-6Al-4V alloy is diffused with zirconium at high temperature using a conventional diffusion process. The alloy is then oxidized to form mixed oxides of titanium, zirconium, aluminum and potentially vanadium.

Figure 6:
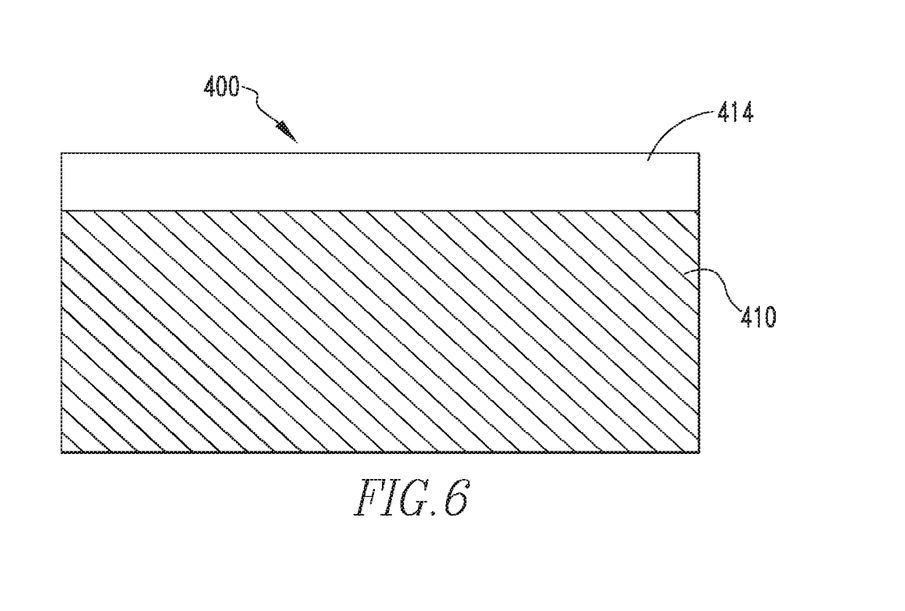
FIG. 6 is a schematic of a zirconium alloy surface alloyed with titanium and subsequently oxidized.

FIG. 6 illustrates yet another embodiment of the invention. The embodiment depicted in FIG. 6 is a structure 400 having a substrate 410 and a surface alloyed zone 414. In FIG. 6, a mixture of oxides, nitrides, carbides or any combinations thereof covers a substrate of zirconium alloy. For example, the mixture may be formed by diffusing titanium into a zirconium substrate. The thickness of the mixed oxides is generally from about 1 micron to about 100 microns. Then the entire sample is oxidized. Diffusion of titanium in the zirconium substrate results in the formation of a much thicker oxide on the surface than it would have formed otherwise on a non-alloyed zirconium surface. The treated alloy can then be further diffusion hardened with a vacuum treatment to increase the depth of hardening.

In another embodiment of the invention, chromium is diffused into a cobalt chrome substrate and then the surface is nitrided to form a chromium nitride or is oxidized to form chromium oxide.

In some embodiments of the invention, the alloyed surfaces may be oxidized or nitrided or carburized in-situ such as during the alloying process. In some embodiments of the invention, a medical implant may include an alloyed surface that has not been oxidized, nitrided, or carburized.

It should be noted that the diffusion process described here is a non-exhaustive, illustrative example of the formation of an alloyed surface. Other techniques such as use of lasers or any other focused energy source such as induction heating to heat or partially melt the surface and then alloy the surface simultaneously using a metal powder jet may be used to create such an alloyed surface. Such embodiments are within the scope of the present invention.

In some embodiments, an inert gas or a mixture of inert gasses may be used during the diffusion hardening process instead of carrying the process out in a vacuum. Inert gasses may include, but are not limited to, nitrogen, argon, helium, krypton and neon.

Figure 7:
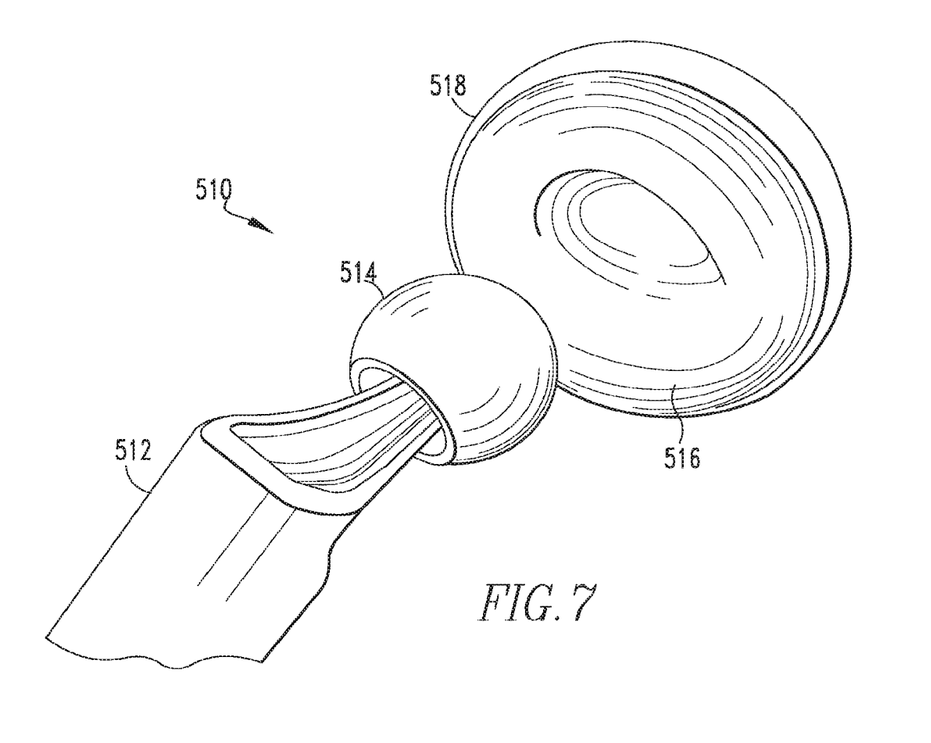
FIG. 7 is a schematic of a hip implant.

The new composition has application in medical implants of all varieties. One of the uses of such an article is a hip implant. FIG. 7 illustrates a hip prosthesis 510. The hip prosthesis 510 includes a stem 512, a femoral head 514, a liner 516, and a shell 518. The femoral head 514 is operatively connected to the stem 512, and the liner 516 is coupled to the shell 518. The stem 512 is adapted for mounting in a femur (not shown), and the shell 518 is adapted for mounting to an acetabulum (not shown). The femoral head 514 articulates against the liner 516. In this particular case, both femoral head 514 and liner 516 can be made of the composition described herein.

In some embodiments of the invention, only one of the articulating components is made from the composition described and the other articulating component is made from a biocompatible material.

The present composition is applicable for any and all medical implants, but in particular for articulating medical implants such as, but not limited to, hip, knee, shoulder, and elbow orthopedic implants. Vertebral implants are also amenable to the present invention. The present invention also finds applicability to any and all non-articulating medical implants.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. For example, while FIG. 3 illustrates a substrate made from Zr-2.5 Nb alloy, other substrate materials may equally be used. Thus, the breadth and scope of the present invention should not be limited by any of the above-described exemplary embodiments, but should be defined only in accordance with the following claims appended hereto and their equivalents.

The invention claimed is:

1. A method for forming a medical implant, said method comprising the steps of:
    providing a substrate comprising a first biocompatible metal;
    diffusing at least a second biocompatible metal into the first biocompatible metal to form a surface alloyed zone, the diffusion occurring at least at the surface of said substrate; and
    diffusion hardening at least a portion of said surface alloyed zone to form a hardened zone, wherein at least a portion of said hardened zone is within at least a portion of said surface alloyed zone.

2. The method of claim 1, wherein said hardened zone comprises a ceramic layer that is formed by diffusion hardening at least a portion of said surface alloyed zone with diffusion hardening species selected from the group consisting of carbon, nitrogen, oxygen, boron, and any combination thereof.

3. The method of claim 1 wherein said step of diffusing the second biocompatible metal is performed in a vacuum of less than $10^{-4}$ Torr and in the temperature range of about 600° C. to about 1200° C.

4. The method of claim 1, wherein said diffusion hardening step is performed in presence of a gas selected from the group consisting of oxygen, nitrogen, and carbon.

5. The method of claim 1, further comprising the step of:
    removing a portion of said second biocompatible metal, said step of removing is selected from the group consisting of grinding, tumbling, glass-beading, shot-peening, grit blasting, polishing, sanding, and abrasive slurry.

6. The method of claim 1, wherein said step of diffusing the second biocompatible metal is performed in an inert gas atmosphere.

7. The method of claim 6, wherein said inert gas is selected from the group consisting of argon, helium, nitrogen, and any combinations thereof.

8. The method of claim 1, wherein said second biocompatible metal is in powder form.

9. The method of claim 1, wherein said step of diffusing the second biocompatible metal comprises:
    placing said second biocompatible metal in contact with said first biocompatible metal; and
    treating said first and second biocompatible metals with focused energy.

10. The method of claim 9, wherein said focused energy comprises use of a laser.

11. The method of claim 9, wherein said focused energy comprises use of induction heating.

\* \* \* \* \*